US00PP24578P3

(12) United States Plant Patent
Coiner

(10) Patent No.: US PP24,578 P3
(45) Date of Patent: Jul. 1, 2014

(54) HYBRID TEA ROSE PLANT NAMED 'JIM JIMMY JAMES'

(50) Latin Name: *Rosa hybrida*
Varietal Denomination: Jim Jimmy James

(76) Inventor: James W. Coiner, Covina, CA (US)

( * ) Notice: Subject to any disclaimer, the term of this patent is extended or adjusted under 35 U.S.C. 154(b) by 64 days.

(21) Appl. No.: 13/573,337

(22) Filed: Sep. 11, 2012

(65) Prior Publication Data

US 2014/0075610 P1 Mar. 13, 2014

(51) Int. Cl.
*A01H 5/00* (2006.01)

(52) U.S. Cl.
CPC ..... *A01H 5/00* (2013.01)
USPC ..... Plt./135

(58) Field of Classification Search
CPC ..... A01H 4/00; A01H 5/00; A01H 1/00; A01H 1/04; A01H 1/06
USPC ..... Plt./135
See application file for complete search history.

*Primary Examiner* — Annette Para
(74) *Attorney, Agent, or Firm* — Christie, Parker, Hale, LLP

(57) ABSTRACT

A new variety of Hybrid Tea rose suitable for garden decoration, having flowers of orange coloration.

1 Drawing Sheet

Classification: The present invention relates to a new *Rosa hybrida* plant.

Variety denomination: The new plant has the varietal denomination 'JIM JIMMY JAMES'.

BACKGROUND OF THE INVENTION

This invention relates to a new and distinct variety of Hybrid Tea Rose. It has as its seed parent the variety known as unknown seedling and as its pollen parent the variety known as unknown seedling.

SUMMARY OF THE INVENTION

Among the features which distinguish the new variety from other presently available and commercial rose cultivars known to the inventor are the following combination of characteristics: The plant has a compact upright growing growth habit, suitable for outdoor garden decoration.

Asexual reproduction of the new variety by budding as performed in Kern County shows that the foregoing and other distinguishing characteristics come true to form and are established and transmitted through succeeding asexual propagations. 'Jim Jimmy James' may be asexually propagated by cuttings, budding and grafting. The budding and grafting successfully occurred on the plant/rootstock *Rosa hybrida* cv. 'Dr. Huey' (unpatented).

COMPARISON WITH THE CLOSEST COMMERCIALLY AVAILABLE CULTIVAR

The new variety may be distinguished from its closest commercially available cultivar, 'STRIKE IT RICH®' (U.S. Plant Pat. No. 19,144) by the following combination of characteristics: darker red on the tips and pronounced notches on the blossoms on deep green foliage.

BRIEF DESCRIPTION OF ILLUSTRATION

The accompanying photograph [FIG. 1] illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 2 year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes usually bears its flowers singly, sometimes usually in clusters of two to five. Flowers are borne in irregular rounded clusters on strong long stems (about 50 to about 60 cm). Outdoors, the plant blooms nearly continuously during the growing season. The flowers have a slight tea fragrance.

BUD

The peduncle is about 3.5 cm to about 6.0 cm in length, of heavy caliper (about 3 mm to about 5 mm in diameter), and usually erect. It is usually rough, with few stipitate glands, and few hairs and prickles. Peduncle color is near between 144a and 148a.

Before the calyx breaks, the bud is about 1 cm to about 2 cm in diameter at the widest point, about 1.2 cm to about 2.5 cm in length, ovoid in shape, with a conspicuous neck. The surface of the bud bears some foliaceous appendages stipitate glands and glandular bloom, usually with slender bristle-like foliaceous parts extending beyond the tip of the bud about one half or more of its length. Bud color is near between 144a and 138a.

The sepals are about 2.8 cm to about 4.2 cm in length and about 1 cm to about 1.5 cm in width at the widest point. The outer surface color of the sepal is near 144a and 138a. The inner surface color of the sepal is near between 137c and 138b and has covered edges with fine wooly tomentum; sepal margins are lined with some stipitate glands and hairs.

The receptacle of the flower is somewhat short in length (about 5 mm to about 7 mm). The receptacle is ovoid in form. Its surface is somewhat smooth with somewhat thin walls. The receptacle color is near between 144a and 138b.

As the petals open (after the calyx breaks), the bud is about 2 cm to about 2.8 cm in diameter at the widest point, about 3.5 cm to about 4.2 cm in length, and somewhat ovoid in form. The color of the under surfaces is close to 26a and 26b at the base, fusing close to 41c and 41d at the apexes. The color of the upper surfaces of the newly opened petals is close to 26a and 26b at the base, fusing close to 41c and 41d at the apexes.

BLOOM

When fully open, the bloom ranges from about 10 cm to about 13 cm in diameter. Petalage is double with about 25 to 30 petals and about 4 to 8 petaloids irregularly arranged. When partially open, the bloom form is somewhat flat to cupped, and the petals are loosely cupped to undulate with petal edges moderately rolled outward. When fully open, the bloom form is somewhat flat to cupped, and the petals are imbricated with petal edges somewhat rolled outward.

PETALS

The substance of the petals is somewhat crisp and of medium thickness, with upper surfaces slightly satiny and under surfaces slightly satiny. The petals are about 4.2 cm to about 6.2 cm in length and about 4.1 cm to about 6.1 cm in width at the widest point. Petal margins are very somewhat serrate.

The outer petals are nearly round to ovate to obovate in shape with apexes somewhat rounded usually slightly notched with one to two notches.

The inner petals are nearly round to ovate in shape with apexes somewhat rounded usually slightly notched with one to two notches.

Petaloids are about 0.5 cm to about 1 cm in length and about (0.4 cm to about 8 cm) in width at the widest point. Petaloids are shaped oval to ovate with rounded apexes.

NEWLY OPENED FLOWER

The under and upper surface color of the outer petals is close to 26a and 26b at the base fusing close to 41c and 41d at the apexes.

The under and upper surface is close to 26b and 26c at the base gradually changing to 41d at the apexes.

The under surface color of the inner petals is near between 25c and 20c. The upper surface color of the inner petals is near between 25c and 25b.

The under and upper surface color of the petaloids are similar in coloration to the upper and under surfaces of the intermediate and inner petals.

The general tonality of the newly opened flower is near between 26a and 26b with 41c and 41d at the apexes.

THREE-DAY OLD FLOWER

The under and upper surface color of the outer petals is close to 26a and 26b at the base fusing close to 41c and 41d at the apexes.

The under and upper surface is close to 26b and 26c at the base gradually changing to 41d at the apexes.

The under surface color of the inner petals is near between 25c and 20c. The upper surface color of the inner petals is near between 25c and 25b.

The under and upper surface color of the petaloids are similar in coloration to the upper and under surfaces of the intermediate and inner petal.

On the spent bloom, the petals usually drop off cleanly except for petaloids persist.

In October, in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids or tucked in the calyx. The filaments are of moderately long length (about 0.5 cm to about 1.3 cm) most with anthers. Filaments are between 13b and 12b in color. The anthers are medium for the class and all open approximately at the same time. Anther color is between 23b and 12c when immature and near between 200a and 167b at maturity. Pollen is abundant and between 17c and 15b in color.

FEMALE REPRODUCTIVE ORGANS

Pistils vary in number (average about 90). The styles are moderately uneven, long in length (about 0.5 cm to about 1.2 cm), somewhat thin in caliper, and moderately separated to loosely bunched. Stigma color is near 13c and 12b. Style color is near 1d and 150d. Ovaries are usually enclosed in the calyx.

Hips have not been observed on this variety when grown in Wasco, Calif.

FOLIAGE

The compound leaves are usually comprised of three to five leaflets and are borne in normal quantities. The five-leaflet leaves are about 12.7 cm to about 15.9 cm in length and about 10.3 cm to about 12.8 cm in width at the widest point, moderately crisp in texture with normal thickness, and semi-glossy in finish. The terminal leaflets are about 5.5 cm to about 8.0 cm in length and about 3.2 cm to about 5 cm in width at the widest point, shaped obovate with obtuse apexes and somewhat round bases. Their margins are serrate.

The upper surface color of the mature leaf is near between 137a and 137b. The under surface color of the mature leaf is near between 145a and 145b. The upper surface color of the young leaf is near between 138a and 138b. The under surface color of the young leaf is near between 145b and 145c.

The rachis is average in caliper and rough. The upper side is shallowly grooved with few hairs and stipitate glands and prickles on the edges of the grooves. The under side of the rachis is rough with few hairs and stipitate glands and small to medium prickles. The rachis color is near between 146c and 146b.

The stipules are about 1.2 cm to about 1.4 cm in length and narrow width to wide (about 1 cm to about 1.5 cm) with short to medium points that usually turn out at an angle of less than 45 degrees toward the stem. The stipules color is near between 146c and 146b.

The petiole is average in caliper and rough. The upper side is deeply to moderately shallowly grooved with many hairs and stipitate glands and prickles on the edges of the grooves. The petiole color is near between 146b and 146c.

The plant displays an average degree of resistance to powdery mildew and rust as compared to other commercial varieties grown under comparable conditions in Wasco, Calif. The plant's winter hardiness and drought/heat tolerance are yet to be determined.

GROWTH

The plant has a compact upright medium height growth habit (about 110 to about 125 cm in height and about 60 cm to about 40 cm spread at the widest point), with full branching. It displays vigorous growth and the canes are of medium caliper for the class.

The color of the major stems is near between 148a and 146a. They bear large prickles that are about 0.07 cm to about 1.1 cm in length. The large prickles are almost straight and hooked slightly downward with medium length to rounded base; prickle color is near 166d. The major stem bears few prickles of similar shape and coloration. There are few fine hairs of similar shape and coloration which are near between 166c and 166d.

The color of the branches is near between 148a and 146b. They bear few large prickles which are of similar size and shape to the large prickles on the major stems; prickle color is near 166c. The branches bear few prickles of similar shape and coloration and which are near 166c.

The color of the new shoots is near between 144a and 148b. They bear few prickles which are of similar size and shape to the large prickles on the major stems; prickle color is near 166c.

I claim:

1. A new and distinct Hybrid Tea rose plant of the variety substantially as described and illustrated herein.

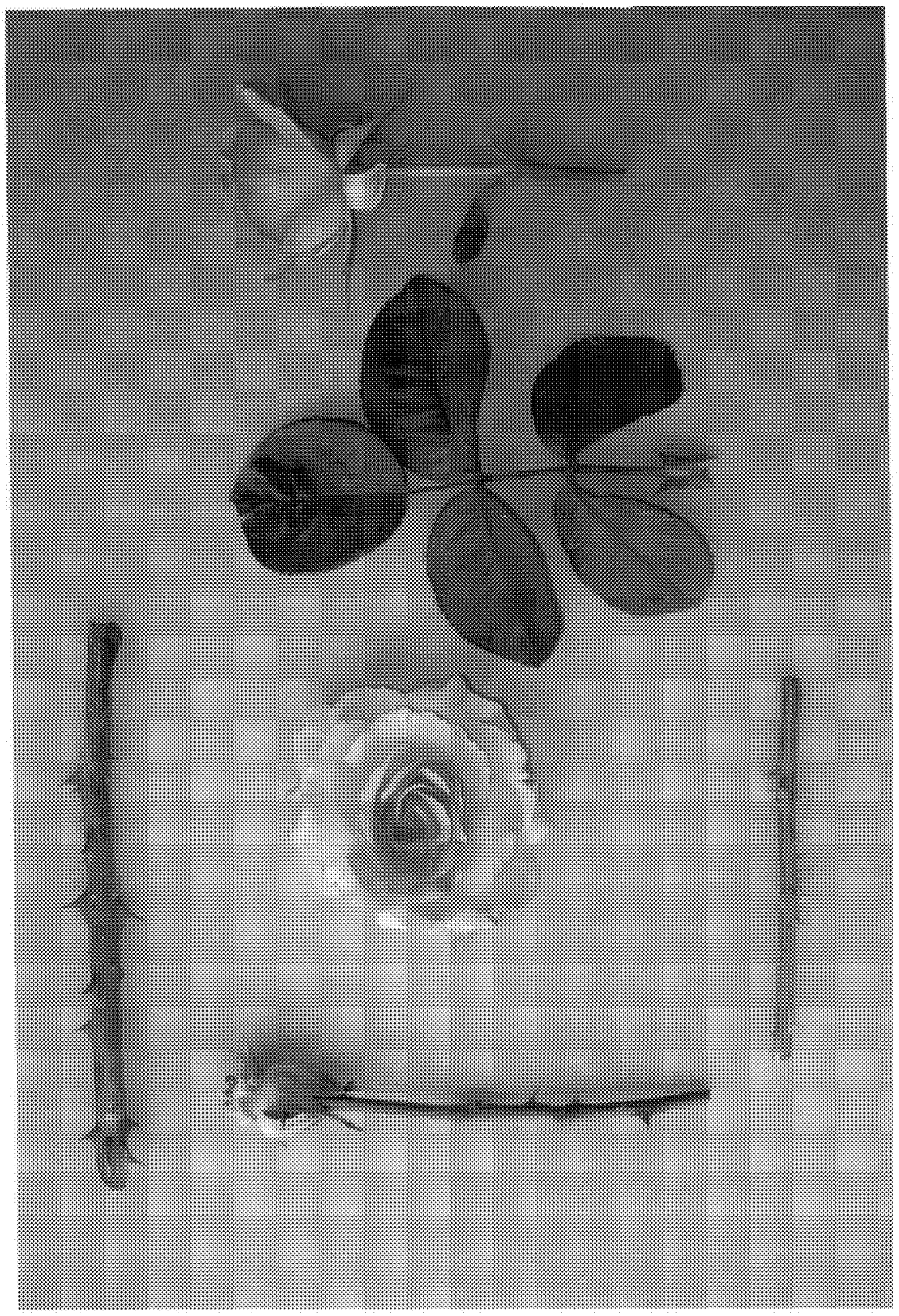

* * * * *